United States Patent
Stango et al.

(10) Patent No.: US 9,259,292 B1
(45) Date of Patent: Feb. 16, 2016

(54) ADJUSTABLE DENTAL PROPHYLAXIS ANGLE WITH ROTATING ADJUSTER

(71) Applicant: HU-FRIEDY MFG. CO., LLC, Chicago, IL (US)

(72) Inventors: James Christopher Stango, Chicago, IL (US); Charles Jerome Saslow, Highland Park, IL (US); Rachel Calian Trautvetter, Evanston, IL (US); Karen Leigh Neiner, Chicago, IL (US); Steven Rodney Walding, Chicago, IL (US); Albert Anthony Schenk, III, Trevor, WI (US)

(73) Assignee: HU-FRIEDY MFG. CO., LLC, Chicago, IL (US)

( * ) Notice: Subject to any disclaimer, the term of this patent is extended or adjusted under 35 U.S.C. 154(b) by 0 days.

(21) Appl. No.: 14/606,639

(22) Filed: Jan. 27, 2015

(51) Int. Cl.
*A61C 1/12* (2006.01)
*A61C 17/00* (2006.01)

(52) U.S. Cl.
CPC ................ *A61C 1/12* (2013.01); *A61C 17/005* (2013.01)

(58) Field of Classification Search
CPC ................................ A61C 17/005; A61C 1/12
USPC ......... 433/103, 114, 112, 124, 125, 130, 133; 15/28; 81/57.27, 57.26
See application file for complete search history.

(56) References Cited

U.S. PATENT DOCUMENTS

| | | |
|---|---|---|
| 219,849 A | 9/1879 | Cushing |
| 636,476 A | 11/1899 | Webster |
| 1,170,524 A | 2/1916 | Fernald |
| 1,379,880 A | 5/1921 | Seaborn |
| 4,278,429 A | 7/1981 | Straihammer et al. |
| 4,303,393 A | 12/1981 | Gentry |
| 5,150,495 A | 9/1992 | Discko, Jr. et al. |
| 5,433,605 A | 7/1995 | Strobl, Jr. |
| 5,699,810 A * | 12/1997 | Pallikaris ...................... 128/898 |
| 5,902,107 A | 5/1999 | Lowell |
| 6,050,989 A | 4/2000 | Fox et al. |
| 6,053,732 A | 4/2000 | Sale |
| 6,168,433 B1 * | 1/2001 | Hamlin .................. A61C 1/185 433/125 |
| 7,422,433 B2 | 9/2008 | Carron et al. |
| 8,123,523 B2 | 2/2012 | Carron et al. |
| 8,360,774 B2 | 1/2013 | Carron et al. |
| 8,459,992 B2 | 6/2013 | Carron et al. |
| 8,597,022 B2 | 12/2013 | Carron et al. |
| 8,668,494 B2 | 3/2014 | Carron et al. |
| 8,814,566 B2 | 8/2014 | Carron et al. |
| 8,834,159 B2 | 9/2014 | Carron et al. |
| 2007/0233567 A1 | 10/2007 | Daly |
| 2008/0220392 A1 | 9/2008 | Carron et al. |
| 2010/0015568 A1 | 1/2010 | Carron et al. |
| 2012/0214126 A1 * | 8/2012 | Carron et al. .................. 433/125 |
| 2015/0335395 A1 | 11/2015 | Boehm |

FOREIGN PATENT DOCUMENTS

| | | |
|---|---|---|
| WO | WO-2008109750 A2 | 9/2008 |
| WO | WO-2009043059 A1 | 4/2009 |

* cited by examiner

*Primary Examiner* — Edward Moran
(74) *Attorney, Agent, or Firm* — Marshall, Gerstein & Borun LLP

(57) ABSTRACT

An adjustable dental prophylaxis angle includes an adjuster operatively coupled to a hand piece and a tool head such that the adjuster can rotate axially relative to the hand piece and to the tool head. The angle of the tool head relative to the hand piece may be adjusted by rotating the adjuster.

17 Claims, 2 Drawing Sheets

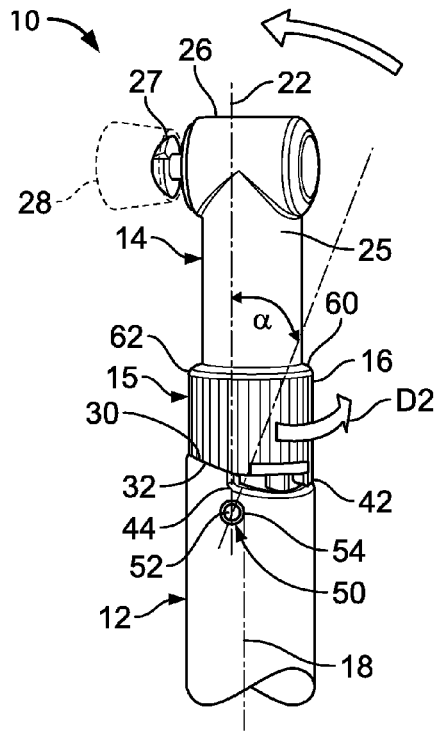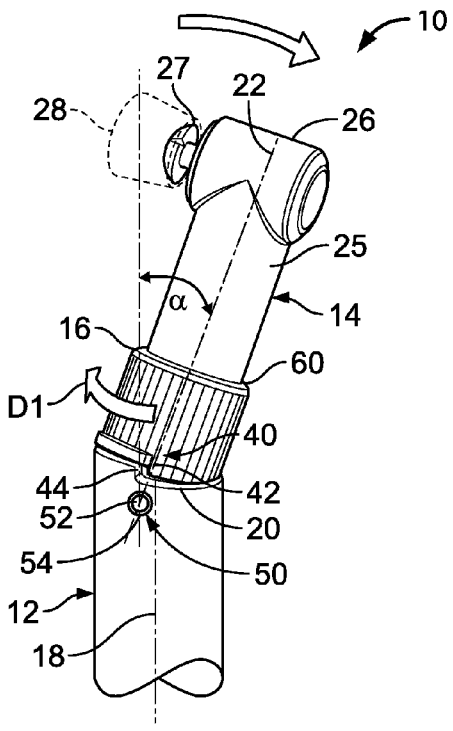
FIG. 2  FIG. 3
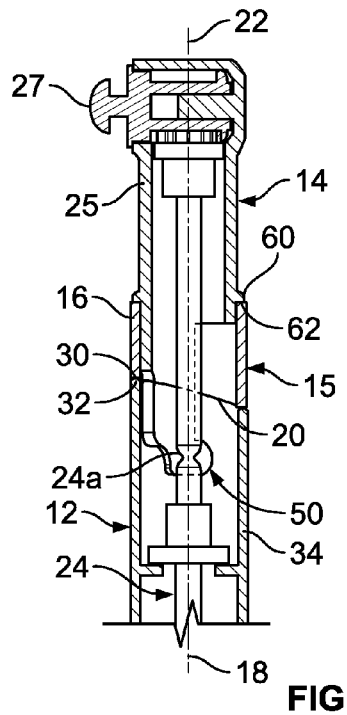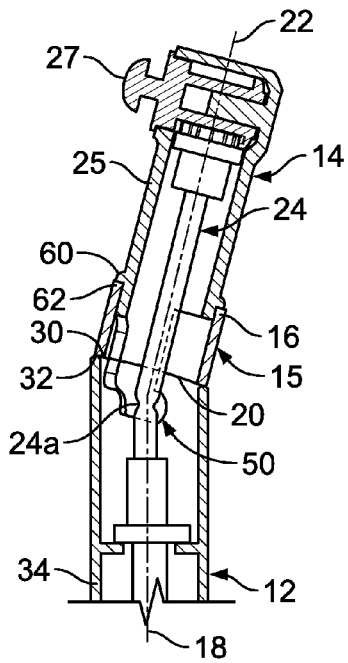
FIG. 4  FIG. 5

ADJUSTABLE DENTAL PROPHYLAXIS ANGLE WITH ROTATING ADJUSTER

FIELD OF THE INVENTION

The present invention relates to a dental prophylaxis angle having an adjustment mechanism to adjust an angle of the tool head relative to the hand piece.

BACKGROUND

A dental prophylaxis angle (also frequently called simply a "prophy angle") is a dental/medical instrument generally having a hand piece to be gripped by a user, such as a dentist or surgeon, and a tool head that carries a tool drive upon which a tool, such as a dental or surgical tool, is or may be mounted. The tool drive is arranged in such manner that the tool extends at an angle, often a right angle, to a longitudinal axis of the hand piece and/or the tool head. Sometimes the hand piece and the tool head are provided in a straight configuration, i.e., coaxially aligned along a single longitudinal axis. Sometimes, the tool head is provided in an angled configuration, i.e., wherein the longitudinal axis of the tool head is angled laterally in relation to the longitudinal axis of the hand piece.

Adjustable prophy angles are known that include an angular adjustment mechanism which allows the tool head to be selectively adjusted angularly, for example, between a straight configuration and an angled configuration. However, the adjustment mechanisms for known adjustable prophy angles are often relatively complex and/or cause or require unwanted movements between the tool head and the hand piece.

SUMMARY

According to one aspect, an adjustable dental prophylaxis angle includes an adjuster operatively coupled to a hand piece and a tool head such that the adjuster can rotate axially relative to the hand piece and to the tool head. The angle of the tool head relative to the hand piece may be adjusted by rotating the adjuster.

In some arrangements, an adjustable dental prophylaxis angle includes a hand piece having a first axis, a tool head pivotably coupled to the hand piece, the tool head having a second axis, and an adjuster operatively coupled to the hand piece and to the tool head so as to rotate axially relative to the hand piece and to the tool head. Rotating the adjuster causes the tool head to pivot angularly relative to the hand piece. In this manner, an angle of the second axis of the tool head relative to the first axis of the hand piece may be adjusted.

The adjustable dental prophylaxis angle may optionally include any one or more of the additional arrangements and/or features either singly or in combination.

In some arrangements, rotating the adjuster in a first direction pivots the tool head from a first position toward a second position relative to the hand piece. Optionally, rotating the adjuster in a second direction opposite the first direction pivots the tool head from the second position toward the first position. In some arrangements the first axis is substantially angularly aligned with the second axis the first position. In some arrangements, the first axis is angularly offset from the second axis in the second position. However, the first position in the second position may have other angular alignments, for example, as described variously herein.

In some arrangements, the adjuster includes a cam that slidingly engages a cam follower. One of the cam and the cam follower is carried by the adjuster. The other of the cam and the cam follower is carried by at least one of the hand piece and the tool head. The cam may be carried by the adjuster. The cam follower may be carried by the hand piece and/or by the tool head. In any arrangement, the cam and the cam follower are arranged such that, when the adjuster is rotated, the cam slides along the cam follower, which causes the tool head to move between the first position in the second position.

In some arrangements, the adjuster is in the form of a collar. The collar may completely or partially surround a portion of one or both of the tool head and the hand piece. The collar may be in the form of a tubular section, such as a ring-shaped cylindrical section. However, the collar may have other shapes. The collar may form an outer peripheral surface of the prophy angle, which may be engaged by a user from the exterior of the dental prophylaxis angle.

In some arrangements, the collar surrounds an axial length of the tool head. The axial length may extend from a proximal end of the housing of the tool head. The collar may be able to rotate around the axial length of the tool head. The tool head may include a peripheral shoulder. The peripheral shoulder may be disposed on an exterior surface of the housing of the tool head. The peripheral shoulder may be disposed at the opposite end of the axial length of the tool head opposite from the proximal end of the housing. A distal end of the collar may abut the peripheral shoulder. A proximal end of the collar may abut a distal end of the hand piece. The collar may be captured between the distal end of the hand piece and the peripheral shoulder. The peripheral shoulder may be in the form of an annular flange extending entirely around an outer surface of the tool head. The peripheral shoulder may be in the form of one or more projections on the tool head.

In some arrangements, the proximal end of the collar may define a cam profile. The distal end of the hand piece may define a cam follower profile. The proximal end of the collar may be axially aligned with the distal end of the housing of the hand piece. The cam profile may slidingly engage the cam follower profile. One or both of the cam profile and the cam follower may be angled between 0° and 90° from the respective first axis and second axis. Preferably, one or both of the cam profile in the cam follower is angle between approximately 60 and 85° from the respective first and second axes. More preferably, one or both of the cam profile and the cam follower is angled between approximately 70 and 75° from the respective first and second axes.

In some arrangements, the dental prophylaxis angle may include one or more stops configured to prevent angular pivoting of the tool head past one or more preselected positions. The stops may take different forms. In one arrangement, a first stop is configured to prevent angular pivoting of the tool head past the second position. The stop may include a first surface of the collar that abuts against a second surface of the hand piece at the second position as the tool head approaches the second position, thereby preventing the collar from rotating further in the first direction past the second position. Where a proximal end of the collar is disposed against the distal end of the hand piece, the first surface may be formed by a first step in the proximal end of the collar and/or the second surface may be formed by a second step in the distal end of the hand piece.

In some arrangements, a pivot pivotably couples the tool head and the hand piece together. The pivot may form a pivot axis extending transversely to one or both of the first axis and the second axis. The pivot axis may extend through one or both of the first axis and the second axis. The pivot axis may be offset from one or both of the first axis and the second axis. The pivot axis may be perpendicular to one or both of the first axis and the second axis. The pivot axes may be formed by a pin that is rotatably received within a socket. The pin may be carried by one of the tool head and the hand piece, and the socket may be defined by the other of the tool head and the hand piece. The pin may extend along the pivot axis transversely to the first axis and the second axis. The socket may be in the form of a blind bore. The socket may be in the form of a through bore. In some arrangements, the pivot may include two such pins disposed on opposite sides of the tool head, and two such sockets defined on opposite sides of the hand piece. The pin or pins are rotatably received within the respective sockets.

Additional aspects and arrangements are apparent upon review of the following description and the accompanying drawings.

BRIEF DESCRIPTION OF THE DRAWINGS

FIG. 2 is a partial side view of the dental prophylaxis angle adjusted to a first position;

FIG. 3 is a partial side view of the dental prophylaxis angle adjusted to a second position;

FIG. 4 is a longitudinal partial cross-sectional view of the dental prophylaxis angle adjusted to the first position shown in FIG. 2; and FIG. 5 is a longitudinal partial cross-sectional view of the dental prophylaxis angle adjusted to the second position shown in FIG. 3.

DETAILED DESCRIPTION OF THE DRAWINGS

Figure 1:
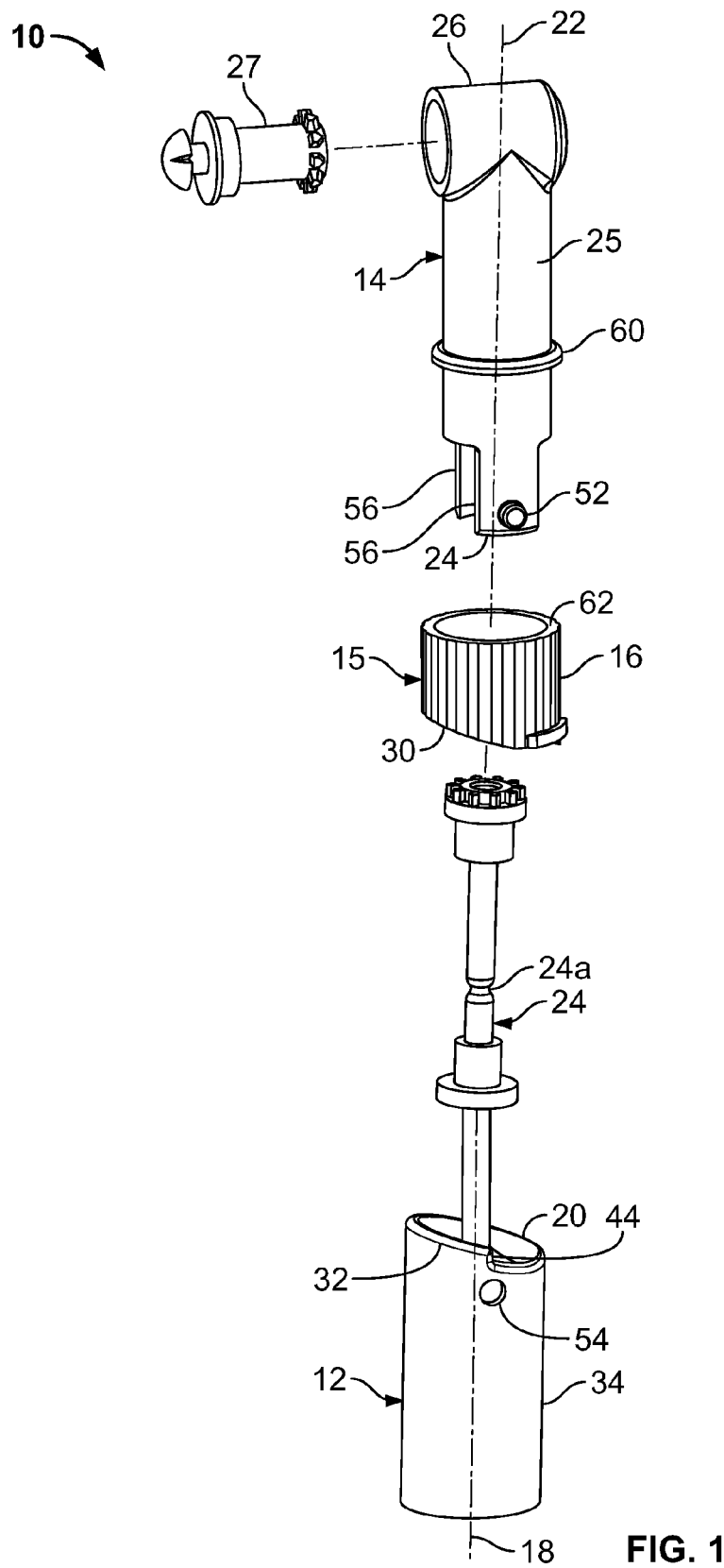
FIG. 1 is an exploded partial perspective view of a dental prophylaxis angle according to one exemplary arrangement.

Turning now to the drawings, an adjustable dental prophylaxis angle 10 (hereinafter, "prophy angle") includes a hand piece 12, a tool head 14 pivotably coupled to the hand piece so as to pivot laterally about a pivot axis, and an angle adjuster 15, which may be in the form of a collar 16, which allows the tool head 14 to be angularly adjusted about the pivot axis among a plurality of angular positions relative to the hand piece 12. The hand piece has a first axis 18, which may extend along and/or be defined by a longitudinal axis of the hand piece 12, for example extending from a proximal end (not shown) to a distal end 20 of the hand piece 12. The tool head 14 has a second axis 22, which may extend along and/or be defined by a longitudinal axis of the tool head 14, for example extending from a proximal end 24 to a distal end 26 of the tool head 14. The adjuster 15 is operatively coupled to the hand piece 12 and to the tool head 14 so as to rotate axially relative to the hand piece and to the tool head. Rotating the adjuster 16 axially causes the tool head 14 to pivot angularly relative to the hand piece 12. Thus, an angle of the second axis 22 of the tool head 14 relative to the first axes 18 of the hand piece 12 can be adjusted by rotating the collar.

In the example of the drawings, the collar 16 is in the form of tubular, preferably cylindrical, wall. The tubular wall is shaped and sized to slidingly surround a housing 25 of the tool head 14 such that the collar 16 can be rotated, e.g., by being twisted by a user's hand, axially about the housing of the tool head 14. However, the angle adjuster 15 need not be limited to the particular form of the collar 16 shown in the figures. For example, the angle adjuster 15 may be in the form of a partial collar that only partially surrounds the housing of the tool head 14. In other arrangements, the adjuster 15 may have another shape that allows the adjuster to be selectively axially rotated around one or both of the axes of the hand piece 12 and the tool head 14. The adjuster 15 need not necessarily surround the tool head 14 or the hand piece 12, or to form a radial outermost surface (as shown in the drawings), but rather needs simply to have a portion that is accessible to the user on the exterior so as to be able rotate the adjuster. Thus, although the following detailed description refers to the collar 16, it is understood that the description applies equally, where functionally possible, to other forms and shapes of the adjuster 15.

The prophy angle 10 also preferably includes other standard parts appropriate for performing the usual functions of a prophy angle. Thus, for example, the prophy angle 10 may also include a drive linkage 24, which operatively connects a drive, such as a motor carried by the hand piece 12 (not shown), to a tool drive 27 carried near the distal end 26 of the tool head 14. The drive linkage 24 preferably is flexible, and thus may include a flexible joint 24a. The flexible joint 24a is preferably aligned with the pivot axis between the hand piece 12 and the tool head 14. The tool drive 27 is adapted to carry a tool 28, such as a polishing tool disposed generally at an angle, such as a 90° angle, from the second axis 22. However, these components and the arrangement thereof in the prophy angle 10 are exemplary only, and other components and/or arrangements suitable for functioning as a prophy angle are contemplated.

As best seen in FIGS. 2 and 3, the collar 16 is operatively arranged such that rotating the collar 16 in a first direction D1 pivots the tool head 14 from a first position as shown in FIG. 2 toward a second position as shown in FIG. 3 relative to the hand piece 12. The collar 16 is also preferably operatively arranged such that rotating the collar 16 in a second direction D2, which is opposite the first direction D1, pivots the tool head 14 from the second position as shown in FIG. 3 toward the first position as shown in FIG. 2. In the exemplary arrangement of the drawings, in the first position, the first axis 18 is substantially angularly aligned with the second axis 22. Thus, the tool head 14 and the hand piece 12 are preferably longitudinally aligned with each other to form a straight longitudinal axis along the hand piece 12 and the tool head 14 in the first position. In the second position, the first axis 18 is angularly offset from the second axis 22. Thus, the tool head 14 is bent at an angle relative to the hand piece 12 in the second position. Preferably, in the second position, the tool head 14 is angularly offset between approximately 1° and approximately 90° from the hand piece 12. In the exemplary arrangement, the second axis 22 is angularly offset an angle α of approximately 17° from the first axis 18. However, the first position and the second position are not limited to the particular angular alignments shown in the drawings and described above, but may have other angular alignments. For example, the tool head 14 in the first position may be bent at a first angle and in the second position may be bent at a second angle relative to the hand piece 12. In addition, in the first position, the tool head 14 may be bent at a first angle to one side of the first axis 18, and in the second position, the tool head 14 may be bent at a second angle to an opposite side of the first axis 18, or the tool head 14 may be axially aligned with the hand piece 12.

The adjuster 15 includes a cam 30 that slidingly engages a cam follower 32. For example, the collar 16 in the exemplary arrangement of the figures includes a cam 30. The cam 30 operatively engages, such as by sliding, a corresponding cam follower 32. In the exemplary arrangement of the figures, the cam follower 32 is defined by the hand piece 12; however, in other arrangements, the cam follower 32 could be defined by the tool head 14. The cam 30 is formed by a cam profile defined by a proximal longitudinal end of the collar 16. In this example, the cam profile is defined by an angled end surface profile of the collar 16. However, the cam 30 may be formed in other ways and is not limited to the angled longitudinal end surface of the collar 16 as shown in the drawings. The cam profile is preferably angle between 90° and 0° relative to the second axis 22. More preferably, the cam follower profile is angle between approximately 60° and 85° from the second axis 22, and even more preferably between approximately 70° and 75° from the second axes 22.

The cam follower 32 in the exemplary arrangement is formed by a cam follower profile defined by a distal longitudinal end of the hand piece 12. In this example, the cam follower profile is defined by an angled end surface profile of a housing 34 of the hand piece 12. The cam follower profile is preferably complementary to the cam profile. Thus, the cam follower profile is preferably angled between 0° and 90° relative to the second axis 22. More preferably, the cam follower profile is angle between approximately 60° and 85° from the second axis 22, and even more preferably between approximately 70° and 75° from the second axes 22. However, the cam follower 32 may be formed by other structures or and other arrangements as long as the cam follower 32 is arranged to operatively engage the cam 30 of the collar 16. Thus for example, the cam follower 32 in other arrangements, could be carried by the tool head 14, and the cam 30 could be arranged at a distal end of the collar 16 to engage such a cam follower. Further, the terms cam and cam follower are used herein interchangeably to refer to opposite ones of a typical cam/cam follower pair, regardless of which of the pair is considered to be the cam and which of the pair is considered to be the cam follower. Thus, it may be that the collar 16 is considered the carry a cam follower whereas the cam may be considered to be carried by the hand piece 12 or the tool head 14. Further, other cam and cam follower arrangements may be used that are sufficient to cause the tool head 14 to pivot angularly relative to the hand piece 12 in response to rotation of the adjuster 15.

One or more stops 40 may be configured to prevent angular pivoting of the tool head 14 past one or more positions relative to the hand piece 12. Thus, in the exemplary arrangement of the drawings, the prophy angle 10 includes a first stop 40 configured to prevent the tool head 14 from pivoting past the second position, as seen in FIG. 3. In this arrangement, the stop 40 is formed by a first surface of the collar that abuts up against a second surface of the hand piece as the tool head 14 moves from the first position into the second position. As best seen in FIG. 2, the first surface is formed by a first step 42 defined by the proximal edge of the collar 16. The second surface is formed by a second step 44 defined by the distal edge of the housing 34. Thus, as the collar 16 is twisted in the first direction D1, the first step 42 approaches and eventually abuts against the second step 44, thereby preventing further rotation of the collar in the first direction. The prophy angle 10 optionally includes a second stop 40 (not visible) configured to prevent the tool head 14 from pivoting past the first position as shown in FIG. 2. The second stop 40 may be substantially similar to the first stop 40, wherein a surface of the collar abuts up against a surface of the hand piece 12 as the tool head moves from the second position into the first position. However, inclusion of the first stop 40 and/or a second stop as described herein is optional. Further, the first stop 40 and the second stop are not limited to the abutting steps 42, 44, but rather may take other forms as well, wherein one surface of the collar 16 engages another surface to prevent the collar from rotating beyond a selected position. In other arrangements, the stop 40 may be in the form of a surface of the tool head 14 that engages one or more surfaces of the hand piece 12 or the collar 16 to prevent the tool head 14 from pivoting beyond a selected position.

A pivot 50 pivotably couples the tool head 14 with the hand piece 12 at the pivot axis. Preferably, although not necessarily, the pivot 50 extends transversely through each of the first axis 18 and the second axis 22. In the exemplary arrangement of the drawings, the pivot axis extends at right angles, i.e., at 90°, to each of the first axis 18 and the second axis 22. In this arrangement, the pivot 50 includes a pin 52 that is pivotably received within a socket 54. The pin 52 may be carried by either one of the tool head 14 or the hand piece 12, whereas the socket 54 may be defined by the other of the tool head 14 and the hand piece 12. In the exemplary arrangement of the drawings, the pin 52 is carried by the tool head 14 near the proximal end 24 of the housing, and the socket 54 is defined near the distal end in the housing 34 of the hand piece 12. Preferably, the pivot 50 in this arrangement includes two such pins 52 disposed on opposite sides of the housing 25 of the tool head 14, and the housing 34 includes two corresponding sockets 54 disposed on opposite sides of the housing to operatively receive the pins 52 therein. The pins 52 and the sockets 54 are preferably aligned along and/or define the pivot axis between the hand piece 12 and the tool head 14. The sockets 54 may be a through bore, as depicted in the drawings, or a blind bore. In addition, portions of the proximal end 24 of the tool head housing 25 between the pins 52 may be cut away to prevent and/or minimize interference between the housing of the tool head 14 in the housing 34 of the hand piece 12 as the tool head 14 pivots between the first position and second position. In this arrangement, the pins 52 may be considered to be carried by tabs or arms 56 extending downwardly from the proximal 24 of the housing 25, wherein the arms 56 are spaced apart by cutout portions of the housing. However, other arrangements for forming a pivot 50 to pivotably couple the tool head 14 with the tool piece 12 may also be used.

The collar 16 is operatively disposed between the distal end 20 of the hand piece 12 and a peripheral shoulder 60 carried by the tool head 14. The collar 16 surrounds an axial length of the housing 25 of the tool head 14, preferably extending from the proximal end 24 of the housing of the tool head 14. The collar 16 is in the form of a tubular section, such as a ring-shaped cylindrical section. The collar 16 forms an outer peripheral surface of the prophy angle 10, which may be engaged by a user from the exterior of the dental prophylaxis angle. A distal end 62 of the collar 16 abuts against the peripheral shoulder 60, which prevents the collar 16 from sliding longitudinally along the tool head 14 toward the distal and 26 of the tool head. The proximal end of the collar 16 engages against the distal end 20 of the hand piece 12, which prevents the collar from sliding longitudinally toward the proximal end of the hand piece 12. Thus, the collar 16 can rotate about the axis 22 of the tool head 14, but is not able to slide in either direction longitudinally along the tool head 14. In the exemplary arrangement of the drawings, the peripheral shoulder 60 is in the form of an outer annular flange that is perpendicular to the second axis 22 of the tool head 14 and the distal and 62 of the collar 16 is correspondingly perpendicular to a longitudinal axis of the collar 16. However, the peripheral shoulder 60 may be formed by other structures, such as one or more projections extending outwardly from a periphery of the housing of the tool head 14.

In use, as the collar 16 rotates in either the first direction D1 or the second direction D2, the distal end 62 of the collar 16 slides against the peripheral shoulder 60, and the cam 30 slides along the cam follower 32, which in this arrangement corresponds to the cam profile defined along the proximal end of the collar 16 and the corresponding cam follower profile defined along the distal and 20 of the housing 34. Thus, movement of the cam 30 along the cam follower 32 causes the tool head 14 to pivot about the pivot 50 toward either the first position or the second position, depending upon which direction D1 or D2 the collar 16 is rotated. As the collar 16 is twisted in the first direction, the first step 42 approaches and eventually abuts the second step 44 when the tool head 14 reaches the second position, thereby preventing the tool head 14 from pivoting beyond the second position. Further, as can best be seen in FIGS. 4 and 5, the drive linkage 24 is able to flex about the flexible joint 24a as the tool head 14 pivots between the first position and the second position. In this way, the tool drive 26 can be driven by the drive linkage 24 in either position.

While the above description has discussed only a first position and a second position of the tool head 14, it is understood that the tool head 14 may be positioned in a near infinite number of positions intermediate the first position in the second position. In some arrangements, the collar 16 may be arranged to advance in incremental units, thereby providing a predefined limited number of positions between the first position in the second position.

The above description of the exemplary arrangement shown in the drawings is solely for purposes of enabling the skilled person to understand, make, and use an adjustable dental prophylaxis angle in accordance with the teachings of the present invention; however invention is not limited to the exact arrangement of features shown in the drawings, but rather may include any arrangement within the scope of the appended claims.

What is claimed:

1. An adjustable dental prophylaxis angle, comprising:
   a hand piece having a first longitudinal axis;
   a tool head pivotably coupled to the hand piece by a pivot, the tool head having a second longitudinal axis and a tool drive, wherein the pivot comprises a pin carried by one of the tool head and the hand piece, and a socket defined by the other of the tool head and the hand piece, wherein the pin is pivotably received within the socket, the pin extends along a pivot axis that is transverse to each of the first longitudinal axis and the second longitudinal axis, and the hand piece and the tool head pivot angularly about the pivot axis in a plane perpendicular to the pivot axis;
   a drive linkage connected to the tool drive to operatively connect the tool drive with a drive carried by the hand piece, the drive linkage having a flexible joint that allows the drive linkage to flex when the tool head pivots relative to the hand piece; and
   an adjuster operatively coupled to the hand piece and to the tool head so as to rotate axially relative to the hand piece and to the tool head,
   wherein rotating the adjuster axially causes the tool head to pivot angularly laterally about the pivot axis relative to the hand piece, whereby an angle of the second longitudinal axis of the tool head relative to the first longitudinal axis of the hand piece is adjustable, wherein rotating the adjuster in a first direction pivots the tool head from a first position toward a second position relative to the hand piece, and wherein rotating the adjuster in a second direction opposite the first direction pivots the tool head from the second position toward the first position.

2. The adjustable dental prophylaxis angle of claim 1, wherein, in the first position, the first longitudinal axis is substantially angularly aligned with the second longitudinal axis.

3. The adjustable dental prophylaxis angle of claim 1, wherein, in the second position, the first longitudinal axis is angularly offset from the second longitudinal axis.

4. The adjustable dental prophylaxis angle of claim 1, wherein the adjuster comprises a cam that slidingly engages a cam follower.

5. The adjustable dental prophylaxis angle of claim 4, wherein the adjuster comprises a collar.

6. The adjustable prophylaxis angle of claim 5, wherein the tool head comprises a peripheral shoulder, and the collar surrounds an axial length of the tool head, wherein a distal end of the collar abuts the peripheral shoulder and a proximal end of the collar abuts a distal end of the hand piece, and
   wherein the collar rotates around the axial length of the tool head.

7. The adjustable dental prophylaxis angle of claim 5, wherein the collar comprises a cam profile at a proximal end of the collar, wherein the cam profile is angled between 0 and 90 degrees from the first axis.

8. The adjustable dental prophylaxis angle of claim 5, wherein the hand piece comprises the cam follower.

9. The adjustable dental prophylaxis angle of claim 8, wherein the cam follower comprises a cam follower profile at a distal end of the hand piece, wherein the cam follower profile is angled between 90 and 0 degrees relative to the second axis.

10. The adjustable dental prophylaxis angle of claim 5, further comprising:
    a first stop configured to prevent angular pivoting of the tool head past the second position.

11. The adjustable dental prophylaxis angle of claim 10, wherein the stop comprises:
    a first surface of the collar; and
    a second surface of the hand piece,
    wherein the first surface abuts against the second surface in the second position to prevent the collar from rotating further in the first direction.

12. The adjustable dental prophylaxis angle of claim 11, wherein a proximal end of the collar is disposed against a distal end of the hand piece,
    wherein the first surface of the collar comprises a first step in the proximal end of the collar, and
    wherein the second surface of the hand piece comprises a second step in the distal end of the hand piece.

13. The adjustable dental prophylaxis angle of claim 7, wherein the cam profile is angled between approximately 60 and 85 degrees from the first longitudinal axis.

14. The adjustable dental prophylaxis angle of claim 7, wherein the cam profile is angled between approximately 70 and 75 degrees from the first longitudinal axis.

15. The adjustable dental prophylaxis angle of claim 9, wherein the cam follower profile is angled between approximately 70 and 75 degrees from the first longitudinal axis.

16. The adjustable dental prophylaxis angle of claim 9, wherein the cam follower profile is angled between approximately 60 and 85 degrees from the first longitudinal axis.

17. An adjustable dental prophylaxis angle, comprising:
    a hand piece having a first longitudinal axis;
    a tool head pivotably coupled to the hand piece by a pivot, the tool head having a second longitudinal axis and a tool drive, wherein the pivot comprises a pin carried by one of the tool head and the hand piece, and a socket defined by the other of the tool head and the hand piece, wherein the pin is pivotably received within the socket, the pin extends along a pivot axis that is transverse to each of the first longitudinal axis and the second longitudinal axis, and the hand piece and the tool head pivot angularly about the pivot axis in a plane perpendicular to the pivot axis;

a drive linkage connected to the tool drive to operatively connect the tool drive with a drive carried by the hand piece, the drive linkage having a flexible joint that allows the drive linkage to flex when the tool head pivots relative to the hand piece; and an adjuster operatively coupled to the hand piece and to the tool head so as to rotate axially relative to the hand piece and to the tool head, wherein the adjuster comprises a cam that slidingly engages a cam follower, wherein rotating the adjuster axially causes the tool head to pivot angularly laterally about the pivot axis relative to the hand piece, whereby an angle of the second longitudinal axis of the tool head relative to the first longitudinal axis of the hand piece is adjustable.

* * * * *